(12) United States Patent
Cohen (10) Patent No.: US 6,280,962 B1
(45) Date of Patent: *Aug. 28, 2001

(54) WHOLE BLOOD/MITOGEN ASSAY FOR THE EARLY DETECTION OF A SUBJECT WITH CANCER AND KIT

(75) Inventor: Tamar Jehuda Cohen, Rehovot (IL)

(73) Assignee: Yoreh Biotechnologies Ltd., Moshav Gimzo (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/766,521

(22) Filed: Dec. 13, 1996

Related U.S. Application Data (63) Continuation-in-part of application No. 08/275,933, filed on Jul. 15, 1994, now Pat. No. 5,637,453, which is a continuation of application No. 08/095,824, filed on Jul. 21, 1993, now abandoned, which is a continuation of application No. 07/797,730, filed on Nov. 25, 1991, now abandoned.

(51) Int. Cl.⁷ ................................................. G01N 33/574

(52) U.S. Cl. ........................................ 435/7.23; 435/7.24

(58) Field of Search .................................. 435/7.23, 7.24

(56) References Cited

U.S. PATENT DOCUMENTS

| | | |
|---|---|---|
| 5,221,610 | 6/1993 | Montagnier et al. . |
| 5,478,724 | 12/1995 | Morse et al. . |
| 5,576,176 | 11/1996 | Adams et al. . |
| 5,637,453 * | 6/1997 | Jehuda-Cohen ......................... 435/5 |

FOREIGN PATENT DOCUMENTS

| | | |
|---|---|---|
| 195 15 219 A | 10/1996 | (DE) . |
| 0203 403 A | 12/1986 | (EP) . |
| WO93/11435 A | 6/1993 | (EP) . |
| WO 93 14189 A | 7/1993 | (EP) . |

OTHER PUBLICATIONS

Hofmann, et al., "Lymphocyte transformation response to pokeweed mitogen as a predictive marker for development of AIDS and AIDS related symptom in homosexual men with HIV antibodies", *British Medical Journal*, vol. 295, pp. 293–295 (Aug. 1, 1987).

Loche, et al., "Identification of HIV-infected seronegative individuals by a direct diagnostic test based on hybridisation to amplified viral DNA", *The Lancet*, pp. 418–421 (Aug. 20, 1988).

Saito, et al., "Detection of HTLV-1 Genome in Seronegative Infants Born to HTLV-1 Seropositive Mothers by Polymerase Chain Reaction", *Jpn. J. Cancer Res.*, vol. 80, pp. 808–812 (Sep. 1989).

Steckelberg, et al., "Subspecialty Clinics" Infectious Diseases –Seronegative Testing for Human Immunodeficiency Virus Antibodies", *Mayo Clin. Proc.*, vol. 63, p. 373–380 (1988).

Stramer, et al., "Markers of HIV Infection Prior to 1gG Antibody Seropositivity", JAMA, Clinical Investigation, vol. 262, No. 1, pp. 64–69 (Jul. 7, 1989).

Hofmann, et al., "HIV–Induced Immunodeficiency—Relatively Preserved Phytohemagglutinin as Opposed to Decreased Pokeweed Mitogen Response May be Due to Possibly Preserved Responses Via CD2 Phytohemagglutinin Pathway", *J. Immunol.*, vol. 142, No. 6, pp. 1874–1880 (Mar. 15, 1989).

Serke, et al., "Lymphocyte activation by phytohemagglutinin and pokeweed mitogen—identification of proliferating cells by monoclonal antibodies", *Journal of Immunological Methods*, vol. 99, pp. 167–172 (1987).

Amadori, et al., "HIV-1 Specific B Cell Activation—A Major Constituent of Spontaneous B Cell Activation during HIV-1 Infection", *The Journal of Immunology*, vol. 143, No. 7, pp. 2146–2152 (Oct. 1, 1989).

Rosenkoetter, et al., "T Cell Regulation of Polyclonally Induced Immunoglubin Secretion in Humans", *The Journal of Immunology*, vol. 132, No. 4, pp. 1779–1783 (Apr. 1984).

Levinson, et al., "In vitro IgM rheumatoid–factor production induced by tetanus toxoid", *J. alergy Clin. Immunol.*, pp. 730–736 (Apr. 1988).

Karsh, et al., "In vitro IgM and IgM rheumatoid factor production in response to *Staphylococcus aureus* Cowan I and pokeweed mitogen: the contribution of $CD5^{30}$ (Leu 1) B cells", *Clin. Exp. Immunol.*, vol. 77, pp. 179–183 (1989).

Edelman, et al., "AIDS: a syndrome of immune dysregulation, dysfunction, and deficiency", *The FASEB Journal*, vol. 3, pp. 22–30 (Jan. 1989).

(List continued on next page.)

*Primary Examiner*—Sheela Huff
(74) *Attorney, Agent, or Firm*—Eitan, Pearl, Latzer & Cohen-Zedek (57) ABSTRACT

This invention provides a method of detecting a subject having ovarian or breast cancer, comprising the following steps; a) obtaining a whole blood sample from the subject; b) incubating the whole blood sample in a culture in the presence of a media containing a mitogen, so as to induce polyclonal activation of lymphocytic cells to produce tumor antigen associated antibodies; c) exposing the resultant culture of step b) to an specific tumor antigen, thereby allowing an antigen-antibody immune complex to form; d) detecting the antigen-antibody immune complex of step c); wherein the presence of tumor antigen associated antibody is indicative of the subject having the cancer.

18 Claims, 4 Drawing Sheets

OTHER PUBLICATIONS

Dorsett, et al. "Anti–Lymphocyte Antibodies in Patients with the Acquired Immune Deficiency Syndrome", *The American Journal of Medicine*, vol. 78, pp. 621–626 (Apr. 1985).

Kopelman, et al., "Association of Human Immunodeficiency Virus Infection and Autoimmune Phenomena ", *The American Journal of Medicine*, vol. 84, pp. 82–88 (Jan. 1988).

Golding, et al., "Identification of Homologous Regions in Human Immunodeficiency Virus Igp41 and Human MHC Class II β 1 Domain", *Journal of Experimental Medicine*, vol. 167, pp. 914–923 (Mar. 1988).

Imagaway, et al. "Human Immunodeficiency Virus Type 1 Infection in Homosexual Men Who Remain Seronegative for Prolonged Periods", *The New England Journal of Medicine*, vol. 320, No. 22, pp. 1458–1462 (Jun. 1, 1989).

Wolinsky, et al., "Human Immunodeficiency Virus Type 1 (HIV–1) Infection a Median of 18 Months before a Diagnostic Western Blot", *American College of Physicians— Annals of Internal Medicine*, vol. 111, No. 12, pp. 961–972 (Dec. 15, 1989).

Pahwah, et al., "Influence of the human T–lymphotropic virus–lymphadenopathy–associated virus on functions of human lymphocytes: Evidence for immunosuppressive effects and polyclonal B–cell activation by banded viral preparations", *Proc. Natl. Acad. Sci. USA*, vol. 82, pp. 8198–8202 (Dec. 1988).

Weimer, et al., "B Lymphocyte Response as an Indicator of Acute Renal Transplant Rejection", *Transplantation*, vol. 48, No. 4, pp. 572–575 (Oct. 1989).

Primi, et al., "Sera from Lipopolysaccharide (LPS)–Injected Mice Exhibit Comoplement–Dependant Cytotoxicity against Syngeneic and Autologous Spleen Cells", *Cellular Immunology*, vol. 32, pp. 252–262 (1977).

Thomas, et al, "Functional Analysis of Human T Cell Subsets Defined by Monoclonal Antibodies", *J. Immunol.*, vol. 125, No. 6, pp. 2402–2407 (Dec. 1980).

Stevens, et al., "Regulation of antibody isotype secretion by subsets of antigen–specific helper T cells", *Nature*, vol. 334, pp. 255–258 (Jul. 21, 1988).

Yamauchi, et al. "Suppression of Hepatitis B antibody Synthesis by Factor Made by T Cells from Chronic Hepatitis B Carriers", *The Lancet*, pp. 324–326 (Feb. 13, 1988).

R. Yarchoan, "Mechanisms of B Cell Activation in Patients with Acquired Immunodeficiency Syndrome and Related Disorders", *Journal of Clinical Investigation*, vol. 78, pp. 439–447 (1986).

M. Leroux, "A Whole–Blood Lymphoproliferation Assay For Measuring Cellular Immunity Against Herpes Viruses" *J. Immunol. Methods*, vol. 79, pp. 215–262 (1985).

Böhnlein et al., *Cell*, vol. 53, pp. 827–836, (1988).

Hall and Gordon, "Reproducibility, efficacy, and methodology of mitogen–induced lymphocyte transformations by the whole blood assay", *J. Immunol. Methods.*, vol. 12, pp. 31–38 (1976).

M. Gorrino et al., "Detectoion of Human Immunodeficiency Virus Type 1 by PCR before Seroconversion in High–Risk Individuals Who Remain Seronegative for Prolonged Periods", *Eur. J. Clin. Microbiol. Infect. Dis.*, vol. 13, pp. 271–274, (1994).

M. Bocchieri et al., "Whole blood culture for measuring mitogen induced T cell proliferation provide superior correlations with disease state and T cell phenotype in asymptomatic HIV–infected subjects", *Journal of Immunological Methods*, vol. 181, 233–243, (1995).

T. Spira et al., "Micromethod for Assaying Reverse Transcriptase of Human T–Cell Lymphotropic Virus Type III/ Lymphadenopathy–Associated Virsu", *Journal of clinical Microbiology*, Vo. 25, No. 1, pp. 97–99, (1987).

H. Wedner and C. Parker, "Lymphocyte Activation" *Prog. Allergy*, vol. 20, pp. 195–300 (1976).

T. Han and J. Pauly, "Simplified Whole Blood Method For Evaluating In Vitro Lymphocyte Reactivity of Laboratory Animals", *Clin. Exp. Immunol.*, vol. 11, pp. 137–142 (1972).

K. Doldi et al., "Proliferation and Interferon Production in Whole Blood Samples and Isolated Lymphocyte Preparations", *Journal of Interferon Research*, vol. 5 pp. 55–64 (1985).

C. Nissen et al., "Can Whole Blood Be Used Instead of Separated Low Density Cells for Examination of the Mitogen Response?" *Blut*, vol. 43: pp. 41–46 (1981).

E. Bloemena et al., "Whole–Blood Lymphocyte Cultures", *Journal of Immunological Methods*, vol. 122, pp. 161–167, (1989).

* cited by examiner

SEQUENCE LISTING

<160> NUMBER OF SEQ ID NOS:  3

<210> SEQ ID NO 1
<211> LENGTH: 14
<212> TYPE: PRT

```
<213> ORGANISM: human protein

<400> SEQUENCE: 1

Ser Gly Ser Gly His Gly Val Thr Ser Ala Pro Asp Thr Arg
1               5                   10

<210> SEQ ID NO 2
<211> LENGTH: 17
<212> TYPE: PRT
<213> ORGANISM: human protein

<400> SEQUENCE: 2

Ser Gly Ser Gly Ala Pro Asp Thr Arg Pro Ala Pro Gly Ser Thr Ala
1               5                   10                  15

Pro

<210> SEQ ID NO 3
<211> LENGTH: 9
<212> TYPE: PRT
<213> ORGANISM: human protein

<400> SEQUENCE: 3

Ile Ile Ser Ala Val Val Gly Ile Leu
1               5
```

WHOLE BLOOD/MITOGEN ASSAY FOR THE EARLY DETECTION OF A SUBJECT WITH CANCER AND KIT

This application is a continuation-in-part application of U.S. Ser. No. 08/275,933 filed Jul. 15, 1994, now U.S. Pat. No. 5,637,453, issued Jun 10, 1997, which is a continuation of U.S. Ser. No. 08/095,824, filed Jul. 21, 1993,now abandoned which is a continuation of U.S. Ser. No. 07/797,730 filed Nov. 25, 1991 now abandoned.

Throughout this application, various publications may be referenced by Arabic numerals in brackets. Full citations for these publications may be found at the end of the specification preceding the claims. The disclosures of the publications cited herein are in their entirety hereby incorporated by reference into this application to more fully describe the state of the art to which this invention pertains.

BACKGROUND OF THE INVENTION

Cancer or tumor cells emerge from the "normal" floura of cells in the body (both human and any other animals known to have tumors). Becoming cancerouse/tumorogenic involves cellular changes. While these changes start off as mutations in the genetic code of the cells, the changes in the behavior of the cell stems from changes in protein/protein expression levels/protein expression.

Structures that are unique to the tumor cell are "tumor antigens". Structures that are not unique to the tumor cell yet might be expressed differently or in access amounts on it are considered "tumor associated antigens". It is wrong to concentrate only on the protein sequence (i.e. also the genomic sequence) as the sole source for changes. Sometimes it is the "coating" of the protein with carbohydrates or lipids that determines its antigenicity. If we take for example the MUCIN from the mammary glands, the protein does not change in the tumor cell, yet antibodies are found against it in patients with breast cancer (and sometimes ovarian cancer too). The reason for it, most probably, is that the protein in the normal cell is not exposed at all due to a dense and thick coat of carbohydrate chains (ie. the protein is very heavily glycosylated). In the tumor cell glycosylation is incomplete thus leading to newly exposed protein sequences that serve (or can serve) as new antigens to the immune system.

Thus any structure that appears to the immune system as new can be considered as a tumor antigen. Another general example of a normal protein appearing and serving as a new antigen for the immune system is that of normal proteins appearing in new context, such as embryonic proteins on mature (or adult) cells. Then the new epitopes would be in the interface between the two structures, an interface that forms new forms and structures for the immune system to see and react to.

SUMMARY OF THE INVENTION

This invention provides a method of detecting a subject with cancer, comprising the following steps; a) obtaining a whole blood sample from the subject; b) incubating the whole blood sample in a culture in the presence of a media containing a mitogen, so as to induce polyclonal activation of lymphocytic cells leading to antibody production; c) exposing the resultant culture of step b) to an specific tumor antigen, thereby allowing an antigen-antibody immune complex to form; d) detecting the antigen-antibody immune complex of step c); wherein the presence of tumor specific antibody is indicative of the subject having cancer.

Lastly, this invention provides a kit for the detection of a subject having ovarian or breast cancer.

DETAILED DESCRIPTION OF THE INVENTION

The present invention relates to an improved assay for detecting a subject with cancer or infected with carcinogenic virus. This invention is contemplated for use as: 1) a diagnostic to determine if an individual has cancer; 2) a prognostic indicator, 3) a method to monitor the effectiveness of anti-cancer treatment (or the effectiveness of a new potential anti-cancer drugs or agents), 4) a method to determine re-occurrence after removal or therapy of a tumor in a subject and 5) a method to detect and quantitate Cancer in assays in clinical and research laboratories.

The present invention is useful as a screening assay for the detection of a tumor or cancer in a subject. A positive blood test will serve as an indication that further testing or a more careful and attentive follow-up is necessary.

This invention provides an in vitro method for the detection of tumor antigen associated antibodies in a sample obtained from a subject, comprising the following steps: a) obtaining a whole blood sample from the subject; b) incubating the whole blood sample in a culture in the presence of a mitogen containing media, so as to induce polyclonal activation of lymphocytic cells leading to antibody production; c) exposing the resultant culture of step b) to a tumor antigen, thereby allowing an antigen-antibody immune complex to form; d) detecting the antigen-antibody immune complex of step c); wherein the presence of tumor associated antibodies is indicative of the subject having cancer.

In one embodiment, a sample of leucocytic cells is obtained from the subject and incubated in a culture in the presence of a media containing a mitogen, so as to induce polyclonal activation of lymphocytic cells. In another embodiment a sample of lymphocytic cells is obtained from the subject and incubated in a culture in the presence of a media containing a mitogen, so as to induce polyclonal activation of B lymphocytic cells. In another embodiment a sample of PBMC is obtained from the subject and incubated in a culture in the presence of a media containing a mitogen, so as to induce polyclonal activation of B lymphocytic cells.

In one embodiment the method comprises the following steps: a) obtaining a whole blood sample from the subject; b) allowing the whole blood sample to separate into a plurality of component layers including an interface layer; c) collecting the interface layer from the whole blood sample; d) incubating the interface layer in a culture in the presence of a mitogen containing media, so as to induce polyclonal activation of lymphocytic cells leading to antibody production; e) exposing the resultant culture of step d) to a tumor antigen, thereby allowing an antigen-antibody immune complex to form; f) detecting the antigen-antibody immune complex of step e); wherein the presence of virus specific antibodies is indicative of the subject having cancer.

This invention provides for the collection of the interface layer, also known as the buffy coat (with varying volumes of red cells and plasma) prior to incubation with the mitogen, thereby putting in culture a part of the blood-sample-volume that is enriched in leukocytes. Methods of leukocyte enrichment are known to those skilled in the art. For example, one may directly suction of the buffy coat as the middle layer in the tube or remove first most of the plasma volume and then take the buffy-coat with the remaining plasma. In the alternative, one may lyse the red cells, centrifuge the culture, and collect the leukocytes from the bottom.

Breast cancer means any tumor from any type of tissue found in the breast. Ovarian cancer means any tumor from any type of tissue found in the ovary. As defined herein "tumor antigen associated antibody" means antibodies directed at tumor antigens or tumor associated antigens.

In one embodiment the specific antibodies producing cells are detected. The culture of step b) may result in a supernatant, and the supernatant may exposed to a tumor antigen, thereby allowing an antigen-antibody immune complex to form. Also, leukocytes or cellular fraction of the culture may be used.

In one embodiment, tumor antigens include but are not limited to MUC-1, and HERneu2 p53 is not a specific marker for a specific cancer but could serve as a more general indicator of tumor state/existence. Antibodies can be looked for either against "naked" p53 or against the complexes it forms with products of transforming genes.

Tumor antigens that are needed for the detection of tumor specific antibodies can be in several forms a) the whole cell (of a tumor), can serve as the antigen; b) cellular membranes the product of which can be used as antigens; c) the sequence of unique tumor structure or proteins (or segments of it) can be inserted via vectors to other producing entities (cells, bacteria, yeast, phage), and then individual proteins and structures will be produced; d) if the amino acid sequences of the tumor specific proteins are known, peptide that are fragments of the whole protein (or the whole protein itself) can be biochemically synthesized and used and antigen.

Cancer and tumors includes but is not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Tumor-Associated Antigen (TAAs) are antigens associated with tumor cells that are also present on normal cells but in less amount. Most induced or transplanted experimental animal tumors immunize syngeneic recipients against subsequent challenge with the same tumor but not against transplantation of normal tissues or other tumors. TAAs are particularly well demonstrated by chemical carcinogen-induced tumors, which tend to have individually specific antigens that vary from tumor to tumor, even with tumors induced by the same carcinogen; and by viral-induced tumors, which tend to show cross-reactivity between tumors induced by a given virus. Viral infections may result in "modified self"; ie, new antigens recognized along with or in the context of the major histocompatibility complex.

Tumor antigens are important because: (1) new genetic information introduced by a virus; (2) alteration of genetic function by carcinogens, possible through activation of a proto-oncogene, by which genetic material that is normally inactive (except perhaps during embryonic development) is activated to an oncogene and becomes expressed in the cell phenotype; (3) uncovering the antigens that are normally present on normal cells or "buried" in the cell membrane, through the inability of neoplastic cells to synthesize membrane constituents (eg, sialic acid); and (4) release of antigens that are normally sequestered in the cell or its organelles, through the death of neoplastic cells.

Techniques to demonstrate TAAs in animal tumors include standard tissue transplantation methods, immunofluorscence, cytotoxicity tests using dye uptake or radioisotope release, prevention of tumor growth in vitro or in vivo by exposing the tumor to lymphoid cells or sera from immunized donors, delayed hypersensitivity skin tests, and lymphocyte transformation in vitro.

Evidence for TAAs in human malignant tumors has been shown with several neoplasms, including Burkitt's lymphoma, neuroblastoma, malignant melanoma, osteosarcoma, and some GI carcinomas. Choriocarcinomas in women possess paternally derived histocompatibility antigens that may serve as "tumor-specific" antigens in eliciting an immune response. The complete cure of choriocarcinomas by chemotherapy may be attributable, at least in part, to such an immune response. Unfortunately although they may possess TAAs, apparently not all human tumors are antigenic in the host.

This invention provides a method of detecting a subject with a tumor comprising the following steps: a) obtaining a whole blood sample from the subject; b) incubating the whole blood sample in a culture in the presence of a media containing a mitogen, so as to induce polyclonal activation of lymphocytic cells leading to antibody production; c) treating the cells so as to recover nucleic acid sequences; d) contacting the resulting nucleic acid sequences with single-stranded labeled oligonucleotide primers, the primers being capable of specifically hybridizing with the nucleic acid sequence of the antibody produced as a result of exposure to an tumor antigen, under hybridizing conditions; and e) detecting the presence of the amplification product, the presence thereof being indicative of the subject having cancer.

The cells of step c) may be treated so as to expose nucleic acid sequences of the cell. Methods of exposure are known to those skilled in the art. Alternatively the resulting nucleic acid sequences of step d) may be amplified by a pair of primers which hybridizes to the nucleic acid sequence so as to obtain a double-stranded amplification product. Amplification product may be detected.

In another embodiment primers contact the resulting nucleic acid sequences capable of hybridizing with nucleic acid sequence at the edge of the variable region, under hybridizing conditions and specifically detected.

This invention provides a method of detecting a subject with a tumor, comprising the following steps: a) obtaining a whole blood sample from the subject; b) incubating the whole blood sample in a culture in the presence of a media containing a mitogen, so as to induce polyclonal activation of lymphocytic cells leading to antibody production; c) treating the cells so as to separately recover nucleic acid sequences; d) contacting the resulting nucleic acid sequences with multiple pairs of single-stranded labeled oligonucleotide primers, each such pair being capable of specifically hybridizing with the nucleic acid sequence of the antibody produced as a result of exposure to a tumor antigen, under hybridizing conditions; e) amplifying any nucleic acid sequences to which a pair of primers hybridizes so as to obtain a double-stranded amplification product; f) treating any such double-stranded amplification product so as to obtain single-stranded nucleic acid sequences therefrom; g) contacting any resulting single-stranded nucleic acid sequences with a labeled oligonucleotide probes, being capable of specifically hybridizing with such the tumor antigen associated antibodies antibody, under hybridizing conditions; h) contacting any resulting hybrids with a detectably marked tag which is capable of specifically forming a complex with the labeled-probe, when the probe is present in such a complex, under complexing conditions; and i) detecting the presence of any resulting complexes, the presence thereof being indicative of the subject having cancer.

As defined herein "sample" refers to any sample obtained from an organism. Examples of biological samples include body fluids and tissue specimens. The source of the sample may be derived from such physiological media as blood, serum, plasma, breast milk, pus, tissue scrapings, washings, urine, tissue, such as lymph nodes, or the like.

The subjects may be a mammal, or more specifically a human, horse, pig, rabbit, dog, sheep, goat, monkey, cow, cat, or rodent. In the preferred embodiment the subject is a human.

"Mitogens" as defined herein means any material that activates lymphocytic cells, so as to secrete or produce specific antibodies. In one embodiment the mitogen is a B cell activator, such as pokeweed mitogen, a lectin, a bacterial endotoxin, an antigen, lipid A, or a lymphokine. In another embodiment the mitogen is a superantigen such as a toxin from bacteria which include staphylococci and staphylococci A toxins (30KD toxins), entertoxins A,B,C1,C2,D,E (from Staphylococcus aureus), exotoxins A,B,C, and exfoliative toxin A,B. In another embodiment, the mitogen is a gram-negative LPS sequence. In another embodiment the mitogen is a peptidoglycan from both gram negative and gram positive bacteria, for example, toxic shock syndrome toxin TSST-1, ExFT, MAM, Strep M, or a Gram-negative lipopolysacchride (LPS) sequences. In another embodiment the mitogen is herpesviruses such as Epstein-Barr Virus (EBV), a retrovirus, mouse mammary tumor virus (MMTV), picornvirus(rats) Coxsackie virus, mumps and measles viruses and Mtv virus (1-9,11,13,43). In another embodiment the mitogen is heat shock proteins(HSP). In another embodiment the mitogen is an antibody which includes but is not limited to: Anti CD3 antibodies, Anti TCR (T cell Receptor), Anti IgM, Anti IgD, Anti CD28 in both soluble form or bound. It is contemplated that interleukines, such as IL-4, either alone or in conjunction with additional factors may be added. In another embodiment the mitogen is phorbol ester such as phorbol myristate acetate, PMA with calcium ionophore and IL-4. In another embodiment pharmacological activators (such as diacylglycerol) that work through paths such as the $PIP_2$ derived second messenger path. In another embodiment the mitogen is a lectin including Pokeweed mitogen (PWM) and similar acting mitogens. In the preferred embodiment Pokeweed mitogen is used.

As used herein, "whole blood" means blood collected from an animal or human. The whole blood contains red blood cells which may be lysed while maintaining the viability of the remaining white blood cells. Whole blood may be collected with heparin, EDTA, citrate or any other substance that prevents coagulation and clotting.

In one embodiment, the optimal concentration of mitogen is easily determined without undue experimentation by one of ordinary skill in the art. With regard to the preferred mitogen, pokeweed mitogen, the preferred concentration range is between approximately 1:100 and 1:1600 dilutions of stock PWM. The most preferred concentration range is between approximately 1:200 and 1:1:400 dilutions of stock PWM. The preferred source of the stock PWM is GIBCO, New York, N.Y. The lyophilized PWM is reconstituted with 5 ml of distilled water to make the stock solution.

The concentration of pokeweed mitogen may range from about 0.05–50.0 ul/ml. The concentration range may be from about 0.1–0.5 ul/ml. The preferred concentration is 0.2 ul/ml. If the mitogen is Wheat germ agglutination the concentration range is about 0.1–2.5 ul/ml. If the mitogen is Sac Cowan I mitogen the concentration range is 1:200–1:2000 dilution.

As defined herein, "culture medium" means any medium than can be used to sustain a sample to practice the present invention, including but not limited to RPMI 1640 (GIBCO, New York, N.Y.) with or without fetal calf serum, preferably supplemented with appropriate antibiotics and glutamine. Other culture media which may be used in practicing the present invention include, but are not limited to, Eagles, Dulbecco's, McCoy's, Media 199, Waymouth's media, and serum free medium with or without supplement. In another embodiment the mitogen is without media.

The nucleic acid sequence referred herein may be DNA, RNA or cDNA. Amplification is carried out using the polymerase chain reaction and a single or plurality of primer sets so as to provide PCR products of different lengths. The plurality of primer sets are amplified together by PCR. Each primer set is amplified separately by PCR.

If one employs two different primer sets, the present invention contemplates that the first primer set is capable of generating a product of a length short enough to be essentially transparent to the addition of the addition compounds to the nucleic acid under a defined set of amplification conditions. That is regardless of the efficiency of the covalent addition of addition compounds, the length of the product is sufficient such that amplification product will be detected.

The second primer set is also capable of generating a product of a length long enough to be affected-not completely inhibited but inhibited in part-by the addition of the addition compounds to the nucleic acid of the nucleic acid-containing antibodies with the same amplification conditions as above. This being so the efficiency of the covalent addition of addition compounds will be reflected in the amount of amplification product detected.

Where three different primer sets are used, the present invention contemplates that the first primer set is capable of generating a product of a length short enough to be essentially transparent to the addition of the addition compounds to the nucleic acid under a defined set of amplification conditions. In other words regardless of the efficiency of the covalent addition of addition compounds, the length of the product is sufficient such that amplification product will be detected. The second primer set is also capable of generating a product of a length long enough to be affected-not completely inhibited but inhibited in part-by the addition of the addition compounds to the nucleic acid of the nucleic acid-containing antibodies with the same amplification conditions as above. Again the efficiency of the covalent addition of addition compounds will be reflected in the amount of amplification product detected. The third primer set is capable of generating a product of a length long enough to be completely inhibited by the addition of addition compounds to the nucleic acid of the nucleic-acid containing antibodies. Covalent addition of the addition compounds will be reflected by the complete absence of measurable amplification product.

For example, after amplification, a portion of the PCR reaction mixture can be separated and subjected to hybridization with an end-labeled nucleotide probe, such as a 32P labeled adenosine triphosphate end-labeled probe. In PCR, an end-labeled oligonucleotide probe hybridizes in solution to a region of the amplified sequence and; in the process, reconstitutes a specific endonuclease site. Thus, hybridization of the labeled probe with the amplified sequence yields a double-stranded DNA form that is sensitive to selective restriction enzyme digestion. After restriction with an endonuclease, the resulting samples can be analyzed on a polyacrylamide gel, and autoradiograms of the portion of the gel with the diagnostic labeled fragment can be obtained. The appearance of a diagnostic fragment (e.g. 10–15 bases in length) in the autoradiogram indicates the presence of tumor antigen associated antibodies nucleotide sequences in the PBMCs.

This invention provides a method for the detection of tumor antigen associated antibodies, comprising; a) obtaining a whole blood sample from the subject; b) incubating the whole blood sample in a culture in the presence of a media containing a mitogen, so as to induce polyclonal activation of lymphocytic cells leading to antibody production; c) exposing the cells so as to separately recover nucleic acid sequences of the tumor antigen associated antibody; d) performing reverse transcription of an RNA of a tumor antigen associated antibodies in a sample to produce a DNA copy; e) performing polymerase chain reaction amplification of the DNA to produce a plurality of DNA copies; f) performing hybridization of the DNA copies to a plurality of complementary DNA probes to detect the DNA content of the sample; thereby detecting tumor antigen associated antibodies.

This invention provides a method for amplifying a target RNA sequence in a sample, comprising; a) obtaining a whole blood sample from the subject; b) incubating the whole blood sample in a culture in the presence of a media containing a mitogen, so as to induce polyclonal activation of lymphocytic cells leading to antibody production; c) exposing the cells so as to separately recover nucleic acid sequences of the tumor antigen associated antibody; d) treating the sample in a reaction mixture comprising a first and second primer, wherein the first primer is sufficiently complementary to the target RNA to hybridize therewith and initiate synthesis of a cDNA sequence complementary to the target RNA, and the second primer is sufficiently homologous to the target RNA to hybridize to the cDNA and initiate synthesis of an extension product, and a thermostable DNA polymerase in the presence of all four deoxyribonucleoside triphosphates, in an appropriate buffer, wherein the buffer comprises Mn+2, at a temperature sufficient for the thermostable DNA polymerase to initiate synthesis of an extension product of the first primer to provide a cDNA sequence complementary to the target RNA; e) treating the reaction mixture at an appropriate temperature to provide single-stranded cDNA; f) treating the reaction mixture at an appropriate temperature for the thermostable DNA polymerase to initiate synthesis of an extension product of the second primer to provide a double-stranded cDNA sequence; and g) amplifying the double-stranded cDNA sequence of step e) by a polymerase chain reaction. In a preferred embodiment, the buffer comprises manganese acetate (also written Mn(OAc)2 or Mn(CH3CO2)2). Bicine-KOH (Bicine is N,N-Bis(2-Hydroxyethyl)glycine), and potassium acetate (also written KOAc or KCH3CO2).

"PCR" refers to a process of amplifying one of more specific nucleic acid sequences, wherein (1) oligonucleotide primers which determine the ends of the sequences to be amplified are annealed to single-stranded nucleic acid in a test sample, (2) a nucleic acid polymerase extends the 3' ends of the annealed primers to create a nucleic acid strand complementary in sequence to the nucleic acid to which the primers were annealed, (3) the resulting double-stranded nucleic acid is denatured to yield two single-stranded nucleic acids, and (4) the processes of primer annealing, primer extension, and product denaturation are repeated enough times to generate easily identified and measured amounts of the sequences defined by the primers. Practical control of the sequential annealing, extension, and denaturation steps is exerted by varying the temperatuer of the reaction container, normally in a repeating cyclical manner. Annealing and extension occur optimally in the 40° C. to 80° C. temperature range (exact value depending on primer concentrations and sequences), whereas denaturation requires temperatures in the 80° C. to 100° C. range (exact value depending on target sequence and concentration).

DNA amplification procedures by PCR are well known and are described in U.S. Pat. Nos. 4,683,195, 4,683,202, and 4,965,188, each of which is incorporated herein by reference. For ease of understanding the advantages provided by the present invention, a summary of PCR is provided PCR requires two primers that hybridize with the double-stranded target nucleic acid sequence to be amplified. In PCR, this double-stranded target sequence is denatured and one primer is annealed to each strand of the denatured target. The primers anneal to the target nucleic acid at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated. One particular method for minimizing the effects of cross contamination of nucleic acid amplification is described in U.S. Pat. No. 5,035,996, which is incorporated herein by reference.

The PCR technique useful for determining whether seropositive or seronegative persons have detectable levels of specific antibodies. In PCR techniques, oligonucleotide primers to the specific tumor associated antibody is indicative of the subject having cancer.

Tumor antigen associated antibodies produced complementary to the two 3' borders of the DNA region to be amplified are synthesized. The polymerase chain reaction is then carried out using the two primers, See *PCR Protocols: A Guide to Methods and Applications* [*PCR Protocols: A Guide to Methods and Applications* (1990) Innis, M., Gelfand D., Sninsky, J. and White, T., eds., Academic Press, San Diego]. Following PCR amplification, the PCR-amplified regions of an tumor antigen associated antibodies can be tested for their ability to hybridize to the three specific nucleic acid probes listed above. Alternatively, hybridization of nucleic acid of the tumor antigen associated antibodies to the above nucleic acid probes can be performed by a Southern blot procedure without DNA amplification and under stringent hybridization conditions as described herein. U.S. Pat. No. 5,494,810 Barany, Francis, et al. "Polymerase chain reaction (PCR)" refers to a patented process (described in U.S. Pat. Nos. 4,683,202 and 4,683,195) for the exponential amplification of a specific DNA fragment by utilizing two oligonucleotide primers that hybridize to opposite strands and flank the region of interest in a target DNA are incorporated by reference. Also, those assays disclosed in the disclosures of the following U.S. patents: U.S. Pat. No. 4,459,359 is incorporated by reference.

Choosing PCR primer sequences, preparing PCR reagents and reaction mixtures, and designing and running PCR reactions are well known procedures in the PCR art. In the event that nucleic acid amplification is performed on suspended cells in a standard PCR tube, the cells are treated like any conventional PCR test sample: diluted into reaction mixture shortly before amplification is started, at a total cell number ranging from approximately 100 to approximately $10^6$.

If multiple samples are amplified simultaneously in different tubes, a fresh sampler tip is used to add the missing reagent(s) to each tube, to prevent cross-contamination. After all tubes have been prepared and capped, the standard three-temperature thermal cycle program of denaturation, annealing, and extension for approximately 10 to 40 cycles is performed under thermal cycler microprocessor control. Alternatively, and often preferably, a series of two-temperature cycles can be run wherein annealing and extension are performed at a single temperature, normally optimized for stringent annealing of primer to template. Because reaction rates may be somewhat retarded with cellular preparations as compared to cell-free nucleic acids, it may be necessary to increase the durations of the denaturation, anneal, extend, or anneal-extend cycle segments as much as several-fold from values standard when the test sample contains cell-free nucleic acid. This adjustment is easily performed by looking for conditions which maximize the intensity of the signal seen during amplified nucleic acid detection or which minimize the number of cycles needed to reach a given signal intensity. A similar optimization procedure can be used for MgC12, dNTP, primer, and enzyme concentrations in the reaction mixture, these parameters often show different optima for different targets, and also may be affected when amplification occurs within fixed cells.

Primer pairs of known sequence positioned 10–300 base pairs apart that are complementary to the plus and minus strands of the DNA to be amplified can be prepared by well known techniques for the synthesis of oligonucleotides. One end of each primer can be extended and modified to create restriction endonuclease sites when the primer is annealed to the nucleic acid sequence of specific antibodies. The PCR reaction mixture can contain the DNA of the specific antibodies, the DNA primer pairs, four deoxyribonucleoside triphosphates, MgC12. DNA polymerase, and conventional buffers. The DNA can be amplified for a number of cycles. It is generally possible to increase the sensitivity of detection by using a multiplicity of cycles, each cycle consisting of a short period of denaturation of the DNA of the specific antibodies at an elevated temperature, cooling of the reaction mixture, and polymerization with the DNA polymerase. Oligonucleotide primers and probes are known to those skilled in the art.

Oligonucleotides for use as probes or PCR primers are chemically synthesized according to the solid phase phosphoramidite triester method first described by Beaucage and Carruthers [Beaucage and Carruthers (1981) *Tetrahedron Lett.* 22:1859–1862.] using an automated synthesizer, as described in Needham-VanDenanter [Needham-VanDevanter, D. R., et al., (1984) *Nucleic Acids Res.* 12:6159–6168]. Purification of oligonucleotides is by either native acrylamide gel electrophoresis or by anion-exchange HPLC as described in Pearson, J. D. and Regnier, F. E. [Pearson, J. D., and Regnier, F. E., (1983) *J. Chrom.* 255:137-14976.]. The sequence of the synthetic oligonucleotide can be verified using the chemical degradation method of Maxam, A. M. and Gilbert, W. [Maxam, A. M. and Gilbert, W. *Methods in Enzymology* (1980) Grossman, L. and Moldave, D., eds., Academic Press, New York, 65:499–560. ]. Tavernarakis, N., U.S. Pat. No. 5,569,485 is directed to amplification and detection of tumor antigen associated antibodies nucleic acid is hereby incorporated by reference.

The present invention has applicability to diagnosing a subject having cancer by the amplification and subsequent detection of nucleic acid sequences of anti tumor antigen associated antibodies "Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be amplified or detected preferentially in the presence of other non-target nucleic acid sequences. Amplification techniques have been designed primarily for the detection of specific target sequences. Template specificity is achieved, in most amplification techniques, by the choice of enzyme. Amplification enzymes are enzymes that, under the conditions in which they are used, will process only specific sequences of nucleic acid in a heterogenous mixture of nucleic acid.

In the case of T4 DNA ligase, the enzyme will not ligate the two oligonucleotides where there is a mismatch between the oligonucleotide substrate and the template at the ligation junction. D. Y. Wu and R. B. Wallace. Genomics 4:560 (1989). Finally, Taq polymerase, by virtue of its ability to function at high temperature, is found to display high specificity for the sequences bounded and thus defined by the primers, the high temperature results in thermodynamic conditions that favor primer hybridization with the specific target sequences and not hybridization with non-target sequences. R. K. Saiki in PCR Technology, Principles and Applications for DNA Amplification (H. A. Erlich, Ed.), pp. 7–16 (1989).

Some amplification techniques take the approach of amplifying and then detecting target; others detect target and then amplify probe. Regardless of the approach, the sample containing nucleic acid must be free of inhibitors for amplification to occur at high efficiency.

Amplification "reagents" are defined as those reagents (primers, deoxyribonucleotide triphosphates, etc.) needed for amplification except for nucleic acid and the amplification enzyme. Typically, amplification reagents along with other reaction components are placed and contained in a reaction vessel (test tube, microwell, etc.).

The preferred lysing agent is protease K. Protease K is a proteolytic enzyme from Tritirachium album. It is particularly useful in the present invention because it has no significant DNase activity and, therefore, does not degrade nucleic acid which would prevent amplification. It is also attractive because it is inexpensive and commercially available (e.g., Sigma, St. Louis, Mo., U.S.A., catalogue No. 4914"Proteinase K"). Various treatment conditions using protease K have been found useful. It is preferred that a high concentration of protease K (e.g., 1:5–2:5 mg/ml) be used for short (5–10 minutes) incubation periods to completely degrade cellular and tumor antigen associated antibodies. When lower concentrations of protease K (e.g., 0.5 mg/ml) are used, longer incubation periods (30–60 minutes) are required to achieve the same effect. Other lysis approaches are also contemplated, including lysis by heating.

The present invention also contemplates labeling methods wherein the oligonucleotide probe sequences have at least one label attached or integrated into its structure. Labels are generally intended to facilitate the detection of the tumor antigen. Labels are chosen from the group consisting of enzymes, fluorophores, high-affinity conjugates, chemiphores and radioactive atoms ("radiolabels"). While other labels may be used, the present invention contemplates: 1) the enzymes alkaline phosphatase, beta -galactosidase and glucose oxidase, 2) the affinity conjugate system of biotin-avidin; 3) the fluorophore that is fluorescein; 4) the chemiphore that is luminol; and 5) the preferred radiolabels 3H, 14C and 32P.

"Detections" of PCR-amplified nucleic acid refers to the process of observing, locating, or quantitating an analytical signal which is inferred to be specifically associated with the product of PCR amplification, as distinguished from PCR reactants. The analytical signal can result from visible or ultraviolet absorbance or fluorescence, chemiluminescence, or the photographic or autoradiographic image of absorbance, fluorescence, chemiluminescence, or ionizing radiation. Detection of in situ PCR products involves microscopic observation or recording of such signals. The signal derives directly or indirectly from a molecular "tag" attached to a PCR primer of dNTP or to a nucleic acid probe, which tag may be a radioactive atom, a chromophore, a fluorophore, a chemiluminescent reagent, an enzyme capable of generating a colored, fluorescent, or chemiluminescent product, or a binding moiety capable of reaction with another sequence or particle which directly carries or catalytically generates the analytical signal. Common binding moieties are biotin, which binds tightly to streptavidin or avidin, digoxigenin, which binds tightly to anti-digoxigenin antibodies, and fluorescein, which binds tightly to anti-fluorescein antibodies. The avidin, streptavidin, and antibodies are easily attached to chromophores, fluorophores, radioactive atoms, and enzymes capable of generating colored, fluorescent, or chemiluminescent signals.

RNA is prepared by any number of methods; the choice may depend on the source of the sample and availability. Methods for preparing RNA are described in Davis et al., 1986, Basic Methods in Molecular Biology, Elsevier, N.Y., Chapter 11; Ausubel et al., 1987, Current Protocols in Molecular Biology, Chapter 4, John Wiley and Sons, NY; Kawasaki and Wang, 1989, PCR technology, ed. Erlich, Stockton Press NY; Kawasaki, 1990, PCR Protocols: A guide to Methods and Applications, Innis et al. eds. Academic Press, San Diego, and Wang and Mark, 1990, PCR Protocols: A guide to Methods and Applications, Innis et al. eds. Academic Press, San Diego, all of which are incorporated by reference. As noted above, the probe will be capable of specific hybridization to a specific tumor antigen associated antibody nucleic acid is indicative of the subject having cancer.

Such "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, Ausubel, F., et al., Methods in Enzymology [*Methods in Enzymology* Vol. 152, (1987) Berger, S. and Kimmel, A. ed., Academic Press, New York] or *Hybridization with Nucleic Acid Probes* all of which are incorporated herein by reference.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6 x SSC solution, washing at room temperature with 6 x SSC solution, followed by washing at about 68° C. in a 6 x SSC in a 0.6 x SSX solution.

Hybridization with moderate stringency may be attained for example by: 1) filter pre-hybridizing and hybridizing with a solution of 3 x sodium chloride, sodium citrate (SSC), 50% formamide, 0.1M Tris buffer at Ph 7.5, 5 x Denhardt's solution; 2) pre-hybridization at 37° C. for 4 hours, 3) hybridization at 37° C. with amount of labeled probe equal to 3,000,000 cpm total for 16 hours; 4) wash in 2 x SSC and 0.1% SDS solution; 5) wash 4 x for 1 minute each at room temperature at 4 x at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization in a different "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [Sambrook, et al. (1989) *Molecular Cloning: A Laboratory Manual* (2nd ed.), Cold Spring Harbor Laboratory, Vols. 1–3. ] or Ausubel, F., et al., [Ausubel, F., et al. (1987) *Current Protocols in Molecular Biology*, New York.].

DNA or mRNA o tumor antigen associated antibodies may be detected by Southern blotting, single stranded conformational polymorphism gel electrophoresis (SSCP), PCR or other DNA based techniques, or for RNA species by Northern blotting, PCR or other RNA-based techniques.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, or by the triester method according to Matteucci, et al., [Matteucci, et al. (1981) *Am. Chem. Soc.* 103:3185. ], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 base pairs or more in length is also encompassed for use as a probe.

This invention provides a method of detecting a subject with a tumor, comprising the following steps: a) obtaining a whole blood sample from the subject; b) incubating the whole blood sample in a culture in the presence of a media containing a mitogen, so as to induce polyclonal activation of lymphocytic cells leading to antibody production; c) exposing the resultant culture of step b) to an specific tumor antigen associated antibody, thereby allowing an antibody-tumor antigen immune complex to form; d) detecting the antibody- tumor antigen immune complex of step c); wherein the presence of tumor antigen associated antibodies is indicative of the subject having cancer.

In one embodiment, the culture of step b) results in a supernatant, and the supernatant is exposed to specific tumor antigen associated antibody, thereby allowing an antibody-tumor antigen immune complex to form.

This invention provides a kit for the detection of specific tumor antigen associated antibodies from a subject, comprising: a container for collecting whole blood samples, wherein the container contains a media containing mitogen, effective to induce polyclonal activation of lymphocytic cells leading to antibody production and an assay for the detection of the specific tumor antigen associated antibody.

This invention provides a kit for the detection of specific tumor antigen associated antibodies from a subject, comprising: a vacuum sealed container for collecting whole blood samples, wherein the container contains a media containing mitogen, effective to induce polyclonal activation of lymphocytic cells leading to antibody production.

In one embodiment, a sample of leucocytic cells is obtained from the subject and incubated in a culture in the presence of a media containing a mitogen, so as to induce polyclonal activation of lymphocytic cells. In another embodiment a sample of lymphocytic cells is obtained from the subject and incubated in a culture in the presence of a media containing a mitogen, so as to induce polyclonal activation of B lymphocytic cells. In another embodiment a sample of PBMC is obtained from the subject and incubated in a culture in the presence of a media containing a mitogen, so as to induce polyclonal activation of B lymphocytic cells. Single or multiple antigens may be bound to the container.

In accordance with the present invention, a blood sample is drawn into a test tube, such as a vacutube, containing an effective concentration of a solution of a mitogen, such as pokeweed mitogen. The blood sample to be tested is cultured in vitro in the presence of the pokeweed mitogen. Other activators of B lymphocytic cells or the humoral system which leads to antibody production or secretion and activators of the $Th_2$ type immune response may be used in place of or in addition to the pokeweed mitogen to achieve the same function. After incubation, an aliquot is taken from the top of the fluid and is then assayed for the presence of desired tumor antigen associated antibodies using standard ELISA procedures and/or Western Blot analysis. If the sample is to be assayed at a later date, the blood may be centrifuged and the supernatant fluid may be collected, frozen and stored. Results may be verified utilizing the technique of polymerase chain reaction (PCR)/FACS. The cellular fractions in the container may be used in PCR or ELISPOT.

The method of the present invention includes optionally separating the blood cells from the fluid portion of the blood so that the presence of tumor antigen associated antibodies can be determined. The separation of the blood cells from the fluid portion of the blood can be done by any of several methods well known to those of ordinary skill in the art, including centrifugation, filtration or density gradient. It is to be understood, that the blood cells do not need to be physically separated from the fluid. After incubation of the whole blood with the mitogen, fluid from the top of the blood can easily be extracted and tested for tumor antigen associated antibody. Optionally, the red blood cells can be lysed either by mild osmotic shock or with a mild detergent. In this way, the white blood cells remain viable.

In one embodiment, of the present invention, whole blood is collected in a blood collection tube containing culture medium and mitogen. The blood samples are then incubated with an approximately 1:500 final dilution of pokeweed mitogen at a concentration of $2 \times 10^6$ viable lymphocytes per ml for 1–12 days at 37° C. in a 7% $CO_2$ humidified atmosphere. The blood may be centrifuged and the supernatant fluid is collected immediately and assayed within approximately 1–12 hours or frozen later for testing for reactive specific antibodies by ELISA/ELISPOT and/or Western blot techniques. In the alternative, an aliquot of fluid or cells or cellular components may be taken directly from the sample.

The present invention also includes a kit comprising a blood collection container containing an effective concentration of mitogen therein. The container can optionally contain a culture medium. The preferred container is a test tube. The blood collection container can be plastic, glass, or any other material that is compatible with culturing blood. It is to be understood that the present invention also includes blood containing means other then a blood collection tube including, but not limited to, microtiter plates containing wells in which the blood can be incubated, tissue culture flasks, glass flasks such as an Erlenmeyer flask, and any other container in which the blood can be cultured.

Tumor antigen associated antibody which specifically bind specific tumor antigen are known to those skilled in the art. Further, antibodies mey be used as tags to bind to the tumor antigen. In one embodiment, the antibody is a monoclonal antibody. In another embodiment the antibody is a polyclonal antibody.

The antibody or DNA sequence may be labeled with a detectable marker including, but not limited to: a radioactive label, or a colorimetric, a luminescent, or a fluorescent marker, or gold. Radioactive labels include, but are not limited to $^3H$, $^{14}C$, $^{32}P$, $^{33}P^{35}$, $S^{36}$, $Cl^{51}$, $Co^{57}$, $Co^{59}$, $Co^{59}$, $Fe^{90}$, $Y^{125}$, $I^{131}$, $I^{186}$, and Re. Fluorescent markers include but are not limited to fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid sequence complex may be detected by a second antibody which may be linked to an enzyme, such as alkaline phosphatase or horseradish peroxidase. Other enzymes which may be employed are well known to one of ordinary skill in the art.

The tumor antigens or antibodies may also be labeled using flourescent labels, enzyme labels, free radical labels, or bacteriophage labels, using techniques known in the art. Typical flourescent labels include flourescein isothiocyanate, rhodamine, phycoerythrin, phycocyanin, alophycocyanin, and Texas Red.

Since specific enzymes may be coupled to other sequences by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Types of enzyme immunoassay are the enzyme-linked immunosorbent assay (ELISA), ELISPOT, and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labeling, the bioluminescent compounds including luciferin, luciferase, and aequorin.

Once labeled, the antibody may be employed to identify and quantify immunologic counterparts (antibody or tumor antigenic polypeptide) utilizing techniques well-known to the art. Antibodies include but are not limited to: IgG and subsets, IgA, IgE, IgM, IgD.

The phrase "specifically binds to an tumor antigen associated antibodies" or "specifically immunoreactive with", when referring to the tumor antigen associated antibodies, refers to a binding reaction which is determinative of the presence of the tumor antigen associated antibody. Thus, under designated immunoassay conditions, the specified tumor antigen associated antibody binds to the tumor antigen associated antibody and does not bind in a significant amount to other antibodies present in the sample. Specific binding to an tumor antigen associated antibody under such conditions may require an tumor antigen that is selected for its specificity for a particular protein.

A variety of immunoassay formats may be used to select specific antibodies specifically immunoreactive with a particular protein. For example, solid-phase ELISA immunoassays are routinely used to select monoclonal antibodies specifically immunoreactive with a protein. See Harlow and Lane [Harlow and Lane, (1988) *Antibodies, A Laboratory Manual*, Cold Spring Harbor Publication, New York.] for a description of immuno assay formats and conditions that can be used to determine specific immunoreactivity.

A description of a radioimmunoassay (RIA) may be found in *Laboratory Techniques in Biochemistry and Molecular Biology* [*Laboratory Techniques in Biochemistry and Molecular Biology* (1978) North Holland Publishing Company, New York.], with particular reference to the chapter entitled "An Introduction to Radioimmune Assay and Related Techniques" by Chard. T., incorporated by reference herein.

A description of general immunometric assays of various types can be found in the following U.S. Pat. Nos. 4,376,110 (David et al.) or 4,098,876 (Piasio) and 4,870,003 (Kortright) are incorporated by reference.

The presence or concentration of this antigen-antibody complex is determined to detect or quantitate the presence of tumor antigen associated antibodies in the biological sample.

This invention provides an isolated nucleic acid molecule encoding a peptide having the amino acid sequence SGSGHGVTSAPDTR (SEQ. ID. No. 1). This invention provides an isolated nucleic acid molecule encoding a peptide having the amino acid sequence SGSGAPDTRPAPGSTAP (SEQ. ID. No. 2). This invention provides an isolated nucleic acid molecule encoding a peptide having the amino acid sequence IISAVVGIL (SEQ. ID. No. 3).

This invention provides a nucleic acid sequence of at least 15 nucleotides capable of specifically hybridizing with a sequence of the nucleic acid sequence of SEQ. ID NOs. 1,2, or 3.

This invention provides an antibody directed to peptide SGSGHGVTSAPDTR (SEQ ID NO. 1), SGSGAPDTRPAPGSTAP, (SEQ ID NO. 2), or IISAVVGIL (SEQ ID NO. 3). In one embodiment, the antibody may a monoclonal or polyclonal. The antibody may be tagged. In another embodiment this invention provides a ligand which binds to the peptide.

This invention also provides a method of imaging cancer in a subject which comprises administering to the subject at least one antibody directed against the peptide of SEQ. ID. NO. 1, 2, or 3, capable of binding to the cell surface of the cancer cell and labeled with an imaging agent under conditions so as to form a complex between the monoclonal antibody and the cell surface antigen. This invention further provides a composition comprising an effective imaging amount of the antibody directed against the peptide and a pharmaceutically acceptable carrier.

The peptides can be used to isolate the normal ligand(s) that bind to it. These ligand(s) depending on specificity may be used for targeting, or their serum levels may be predictive of disease status. Knowledge of the antibodies to the peptide sequence is useful for treatment, i.e.immunotoxin therapy or diagnostic either in vitro, i.e. immunohistochmistry or in-vivo diagnostic use, i.e. radiolabelling.

The ligand to the peptide sequence may may carry a specific substance such as a metal ion (iron or zinc or other) into the tumor and thus serve as a means to deliver toxic substances (radioactive or cytotoxic chemical i.e. toxin like ricin or cytotoxic alkylating agent or cytotoxic prodrug) to the tumor. The linkage of the antibody and the toxin or radioisotope can be chemical. Examples of direct linked toxins are doxorubicin, chlorambucil, ricin, pseudomonas exotoxin etc., or a hybrid toxin can be generated ½, with specificity for peptide and the other ½, with specificity for the toxin. Such a bivalent molecule can serve to bind to the tumor and the other ½ to deliver a cytotoxic to the tumor or to bind to and activate a cytotoxic lymphocyte such as binding to the $T_1$–$T_3$ receptor complex. Antibodies of required specificity can also be cloned into T cells and by replacing the immunoglobulin domain of the T cell receptor (TcR), cloning in the desired MAb heavy and light chains; splicing the $U_h$ and $U_L$ gene segments with the constant regions of the α and β TCR chains and transfecting these chimeric Ab/TcR genes in the patients' T cells, propagating these hybrid cells and infusing them into the patient. Specific knowledge of tissue specific antigens for targets and generation of MAb's specific for such targets will help make this a usable approach.

It is possible to produce a toxic genetic chimera such as TP-40 a genetic recombinant that possesses the cDNA from TGF-alpha and the toxic portion of pseudomonas exotoxin so the TGF and portion of the hybrid binds the epidermal growth factor receptor (EGFR) and the pseudomonas portion gets taken up into the cell enzymatically and inactivates the ribosomes ability to perform protein synthesis resulting in cell death.

The kit can detect the presence of an tumor antigen associated antibody specifically reactive with a tumor antigen or an immunoreactive fragment thereof. The kit can include an tumor antigen bound to a substrate, a secondary tumor antigen reactive with the antibody and a reagent for detecting a reaction of the secondary tumor antigen with the antibody. Such a kit can be an antibody capture assay kit, such as an ELISA kit, and can comprise the substrate, primary and secondary antibodies when appropriate, and any other necessary reagents such as detectable moieties, enzyme substrates and color reagents as described above. The antibody capture diagnostic kit can, alternatively, be an immunoblot kit generally comprising the components and reagents described herein. The particular reagents and other components included in the diagnostic kits of the present invention can be selected from those available in the art in accord with the specific diagnostic method practiced in the kit. Such kits can be used to detect the antibody in biological samples, such as tissue and bodily fluid before and after culture obtained from a subject.

This invention provides a kit for the detection of specific tumor antigen associated antibody from a subject, comprising: a vacuum sealed container for collecting whole blood samples, wherein the container contains a media containing mitogen, effective to induce polyclonal activation of lymphocytic cells leading to antibody production.

Detecting the reaction of the antibody (or ligand) with the tumor antigen can be facilitated by the use of an antibody or ligand that is labeled with a detectable moiety by methods known in the art. Such a detectable moiety will allow visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-strepavidin (for light or electron microscopy) and alkaline phosphatase (for biochemical detection by color change). The detection methods and moieties used can be selected, for example, from the list above or other suitable examples by the standard criteria applied to such selections (Harlow and Lane, Antibodies: A Laboratory Manual, Cold Spring Harbor Laboratory, Cold Spring Harbor, N.Y., 1988).

In the present invention, detecting the reaction of the ligand with the tumor antigen can be further aided, in appropriate instances, by the use of a secondary antibody or other ligand which is reactive, either specifically with a different epitope or nonspecifically with the ligand or reacted antibody.

Enzyme immunoassays such as immunofluorescene assays (IFA), photometric assays, enzyme linked immunosorbent assays (ELISA), ELISPOT, and immunoblotting can be readily adapted to accomplish the detection of the specific antibodies. An ELISA method effective for the detection of the tumor antigen associated antibodies can, for example, be as follows: (1) bind the tumor antigen to a substrate; (2) contact the bound tumor antigen with a biological sample, such as a bodily fluid before and after culture or tissue sample or lymphocytes before and after culture containing the antibody; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe the color change.

Where the tumor antigens are labeled, the labels can include radioisotopes, fluorophores, enzymes, luminescers or particles. These and other labels are well known in the art and are described, for example, in the following U.S. Pat. Nos. 3,766,162; 3,791,932; 3,817,837; 3,996,345, and 4,233,402. Assays employing the tumor antigen associated antibodies from the cell lines can be heterogenous, i.e., requiring a separation step, or homogenous. If the assay is heterogenous a variety of separation means can be employed, including centrifugation, filtration, chromatography or magnetism.

Other detection systems which may also be used include those based on the use of protein A derived from *Staphylococcus aureus* Cowan strain I, protein G from group C Streptococcus sp. (strain 26RP66), or systems which employ the use of the biotin-avidin binding reaction.

Another method of immunoenzymatic detection of the presence of is the Western blot. The tumor antigens are separated electrophoretically and transferred to a nitrocellulose membrane or other suitable support. The body fluid to be tested is then brought into contact with the membrane and the presence of the immune complexes formed is detected by the method already described. In a variation on this methods, purified tumor antigen associated antibodies is applied in lines or spots on a membrane and allowed to bind. The membrane is subsequently brought into contact with the body fluid before and after culture to be tested and the immune complexes formed are detected using the previously described techniques.

The presence of specific antibodies in body fluid before and after culture may also be detected by agglutination. Tumor antigen associated antibodies lysates, tumor antigen or purified composition referred to according to this invention, is used to coat, for example, latex particles which form an uniform suspension. When mixed with serum containing specific antigens to the antibodies present, the latex particles are caused to agglutinate and the presence of large aggregates can be detected visually.

Tumor antigen associated antibodies reactive with specific antibodies of tumor antigen can also be measured by a variety of immunoassay methods. For a review of immunological and immunoassay procedures applicable to the measurement of antibodies by immunoassay techniques, see *Basic and Clinical Immunology* 7th Edition [*Basic and Clinical Immunology* 7th Edition D. Stites and A. Terr ed.].

Hemagglutination Inhibition (HI) and Complement Fixation (CF) which are two laboratory tests that can be used to detect tumor antigen associated antibodies by testing for the presence of antibodies.

In vitro diagnostic assays for the detection of tumor antigen associated antibodies.

This invention provides a method of diagnosing a subject with cancer which comprises: a) obtaining a whole blood sample from the subject; b) incubating the whole blood sample in a culture in the presence of a media containing a mitogen, to induce polyclonal activation of lymphocytes; c)

obtaining a nucleic acid sequence from lymphocytes; d) contacting the nucleic acid sequence with a labeled nucleic acid sequence of at least 15 nucleotides capable of specifically hybridizing with the isolated DNA, under hybridizing conditions; and e) determining the presence of the nucleic acid sequence hybridized, the presence of which is indicative of tumor antigen associated antibodies in the subject, thereby diagnosing the subject.

In one embodiment, the DNA sequence from the tumor antigen associated antibodies is amplified before step (b). In another embodiment PCR is employed to amplify the nucleic acid sequence. Methods of amplifying nucleic acid sequences are known to those skilled in the art.

A person of ordinary skill in the art will be able to obtain appropriate DNA sample for diagnosing the subject. The DNA sample obtained by the above described method may be cleaved by restriction enzyme. The uses of restriction enzymes to cleave DNA and the conditions to perform such cleavage are well-known in the art.

In the above described methods, a size fractionation may be employed which is effected by a polyacrylamide gel. In one embodiment, the size fractionation is effected by an agarose gel. Further, transferring the DNA fragments into a solid matrix may be employed before a hybridization step. One example of such solid matrix is nitrocellulose paper.

Similarly, a Northern transfer may be used for the detection of message in samples of RNA or reverse transcriptase PCR and cDNA can be detected by methods described above. This procedure is also well known in the art.

An alternative means for determining the presence specific antibodies produced as a result of infection or exposure of the tumor antigen associated antibodies is in situ hybridization, or more recently, in situ polymerase chain reaction. In situ PCR is descibed in Neuvo et al. [Neuvo, et al. (1993) *American Journal of Surgical Pathology* 17(7), 683–690.], Intracellular localization of polymerase chain reaction (PCR)-amplified tumor antigen cDNA; Bagasra et al. [Bagasra, et al. (1992) *J. New England Journal of Medicine* 326(21): 1385–1391.], Detection of tumor antigen by in situ polymerase chain reaction; and Heniford et al. [Heniford, et al. (1993) *Nucleic Acids Research* 21(14) :3159–3166.], Variation in cellular EGF receptor mRNA expression demonstrated by in situ reverse transcriptase polymerase chain reaction. In situ hybridization assays are well known and are generally described in *Methods Enzymol.* incorporated by reference herein. In an in situ hybridization, cells are fixed to a solid support, typically a glass slide. The cells are then contacted with a hybridization solution at a moderate temperature to permit annealing of target-specific probes that are labeled. The probes are preferably labeled with radioisotopes or fluorescent reporters.

The above described probes are also useful for in-situ hybridization or in order to locate tissues which express this gene, or for other hybridization assays for the presence of this gene or its mRNA in various biological tissues. In-situ hybridization is a sensitive localization method which is not dependent on expression of tumor antigens or native vs. denatured conditions.

Oligonucleotides are 3' end-labeled with [$\alpha$-$^{35}$S]dATP to specific activities in the range of $1\times10^{10}$ dpm/ug using terminal deoxynucleotidyl transferase. Unincorporated labeled nucleotides are removed from the oligo probe by centrifugation through a Sephadex G-25 column or by elution from a Waters Sep Pak C-18 column.

A probe can be identified as capable of hybridizing specifically to its target nucleic acid by hybridizing the probe to a sample treated according the protocol of this invention where the sample contains both target tumor antigen associated antibodies and animal cells (e.g., nerve cells). A probe is specific if the probe's characterstic signal is associated with the tumor antigen associated antibodies DNA in the sample and not generally with the DNA of the host cells and non-biological materials (e.g., substrate) in a sample.

The following stringent hybridization and washing conditions will be adequate to distinguish a specific probe (e.g., a fluorescently labeled DNA probe) from a probe that is not specific: incubation of the probe with the sample for 12 hours at 37° C. in a solution containing denatured probe, 50% formamide, 2×SSC. and 0.1% (w/v) dextran sulfate, followed by washing in 1×SSC at 70° C. for 5 minutes; 2×SSC at 37° C. for 5 minutes; 0.2×SSC at room temperature for 5 minutes, and H$_2$O at room temperature for 5 minutes. Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions.

It will be apparent to those of ordinary skill in the art that a convenient method for determining whether a probe is specific for a tumor antigen associated antibodies nucleic acid utilizes a Southern blot (or Dot blot) using DNA prepared from one or more tumor antigen associated antibodies. Briefly, to identify a target specific probe DNA is isolated from the tumor antigen associated antibodies. Test DNA is transferred to a solid (e.g., charged nylon) matrix. The probes are labeled following conventional methods. Following denaturation and/or prehybridization steps known in the art, the probe is hybridized to the immobilized DNAs under stringent conditions. Stringent hybridization conditions will depend on the probe used and can be estimated from the calculated $T_m$ (melting temperature) of the hybridized probe (see, e.g., Sambrook for a description of calculation of the $T_m$).

For radioactively-labeled DNA or RNA probes an example of stringent hybridization conditions is hybridization in a solution containing denatured probe and 5×SSC at 65° C. for 8–24 hours followed by washes in 0.1×SSC, 0.1% SDS (sodium dodecyl sulfate) at 50–65° C. In general, the temperature and salt concentration are chosen so that the post hybridization wash occurs at a temperature that is about 5° C. below the $T_M$ of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the tumor antigen associated antibodies, as evidenced by the presence of a signal associated with the appropriate target and the absence of a signal from the non-target nucleic acids, is identified. It is further appreciated that in determining probe specificity and in utilizing the method of this invention to detect tumor antigen specific antibodies, a certain amount of background signal is typical and can easily be distinguished by one of skill from a specific signal. Two fold signal over background is acceptable.

Tumor antigen associated antibodies agent screening assays which determine whether or not a drug may used is contemplated in this invention. Such assays comprise incubating whole blood, lymphocytes, such as B cells, or PBMC with the mitogen and the tumor antigen associated antibodies drug and evaluate whether the cell expresses the tumor antigen associated antibodies and determining therefrom the effect of the compound on the activity of such agent.

Alternatively, the anti-tumor antigen associated entibodies agent is administered to the subject and either whole blood, lymphocytes, or PBMC is obtained and incubated with a mitogen.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

EXAMPLE 1

Early Detection Of Ovarian And Breast Cancer

Methods and Materials:

Antibodies extracted from breast cancer tumors, which were bound to tumor cells, have been shown to bind to a Mucin, specifically Muc-1, molecule. Further analysis showed that it the antibody binds to the protein core/ backbone of Mucin-1. No genetic mutations were found in the protein sequence for Mucin-1. The behavior of a normal protein (non mutated) as a foreign antigen was attributed to the deglycosylation of the protein core. Deglycosylation of the protein core may be the reason that Mucin-1 is reconginzed as a foreign antigen. The peptides P1–P3 were designed to cover the immunodominant epitope of the tandem repeat of Mucin-1 which has several configurations and is common to both breast cancer and ovarian cancer.

The peptides that have been used were derived from the tandem repeat of the MUC-1

OC-P1=SGSGHGVTSAPDTR-$NH_2$, (SEQ ID NO. 1)

OC-P2=SGSGAPDTRPAPGSTAP-$NH_2$, (SEQ ID NO. 2)

OC-P3=IISAVVGIL-$NH_2$ (SEQ ID NO. 3)

The first two are soluble in water, the last is very hydrophobic and needs very low pll for disloving it. The first two are bound to Biotin on their Ac side (for technical reasons) the third is not. The level of purity of OC-P1 and OC-P2 is high >95% OC-P3 is only ~60% pure.

Results:

The cohort from which the preliminary data was collected included 15 women that under went surgery due to suspected OC. Control samples (n=21) were made available from the blood donor services. Antibodies were looked for both in serum (IBTs) and in supernatant fluids (IBTc) following culture of lymphocytes for 6–7 days. Three peptides used were designed based on the published sequences of MUC-1 and HER-2neu.

As can be seen in Table 1, based on histopathological findings, 11/15 were found to be malignant. None of the controls had any reaction in the serum or after in vitro culture to any of the three peptides. IBTs and IBTc showed reactivity against at least one peptide in 10/11 cases. When the assays were combined, 11/11 (100%) were antibody positive. All 4 benign cases were IBTs positive, but only one sample was (weakly) positive using IBTc. Though the number of individuals tested is too small for large scale statistical analysis and predictions, the data seems to indicated that by using both assays all tumors could be identified via peptide specific antibodies providing a convenient and practical tool for testing in populations at high risk for OC. The fact that only ¼ benign cases were IBTc prositive while 10/11 did so in the malignant cases could indicate that the IBTc might help in the discrimination of benign versus malignant cases.

TABLE 1

Diagnostic value of the new IBT by diagnostic grading.

| TEST SYSTEM | CANCER | BENIGN | NORMAL |
| --- | --- | --- | --- |
| IBTs (using serum) | 10/11 | 4/4 | 0/21 |
| IBTc (using culture) | 10/11 | 1/4 | 0/21 |
| IBTs + IBTc | 11/11 | 4/4 | 0/21 |

Blood samples were collected from patients undergoing surgery for suspected OC, and from healthy blood donors. Grading was done on the basis of hispathological findings.

Discussion:

The immune responses test for (antibodies) are antigen specific. The antigens chosen for the screen determine the specificity of the test to cancer or to any specific cancer (breast in this case). It has been repeatedly shown that there is a cross reactivity between ovarian and breast cancer, and that some antigens, such as MUC-1, can be used for detection of both. The cross-reactivity is attributed to the fact that both cancers are hormonal sensitive by the same hormones.

Other examples of cancer antigens include HERneu2 in Breast cancer. Women at high risk for BC (in familial BC for example) are able to show, through longitudinal studies that the appearance (or rise) in antibodies against HERneu2 precedes detection by mammography and/or physical examination by hand.

EXAMPLE 2

The present invention provides a simple and early initial screening or detection of a tumor in a subject via the immune system. As the tumor grows, its suppresive effect on the immune system becomes stronger, thus active secretion of antibodies might be very low or even barely detectable. The present invention uncovers the potential of the humoral arm of the immune system which enables detection of the tumor specific antibodies even if production of antibodies are suppressed in vivo. Therefore, acting as a warning signal.

Methods:

Blood and tissue samples (tumor) were taken with consent from ovarian cancer patients. The patients were all women that underwent surgery. Where applicable cystic fluid was colleted.

Whole blood and separated plasma and PBMC were used for the study. Cells were put into culture for 4–6 days with RPMI complete media and 1:200 pokeweed mitogen (PWM) in a 37 C. $CO_2$ incubator. The samples were later tested for antibody anti the peptide using standard peptide ELISA (1 ug/well peptide, blocked by BSA).

Results:

The results are recorded as O.D. readings of the ELISA. Each mark or letter (h=healthy or c=cancer) is one sample tested. The statistical analysis is based on a 95% confidence interval.

Figure 1:
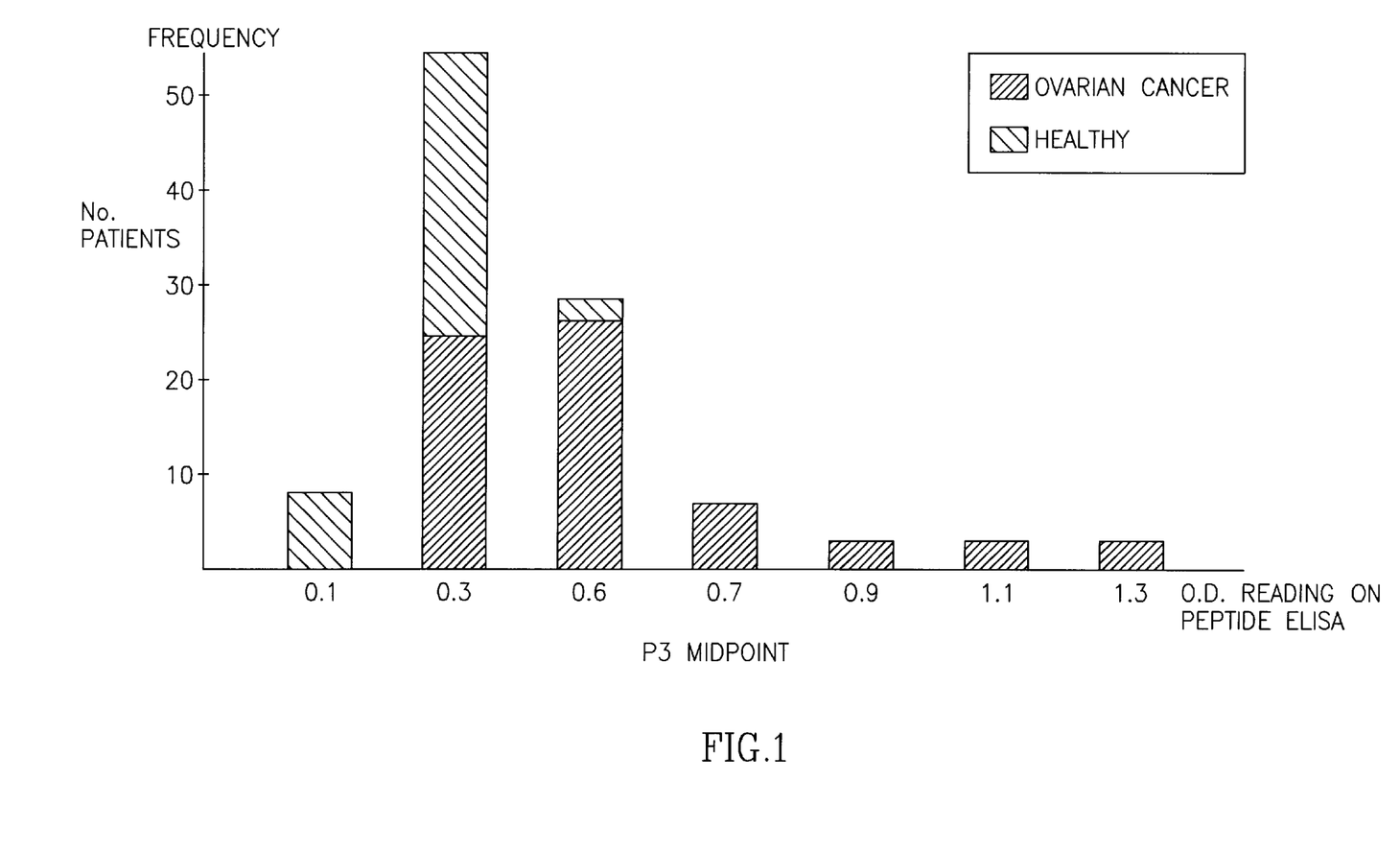
FIG. 1 P3 - One dimensional analysis

FIG. 1: One dimensional analysis—P3

The sample distribution of the O.D. results in two groups c=cancer, h=healthy. As demonstrated there is a trend for higher and more specific sensitivity against the peptide among the cancer patients. However, one dimesional analysis does not appear to be a sufficient as an indicator of the patients having cancer at this size sample.

Figure 2:
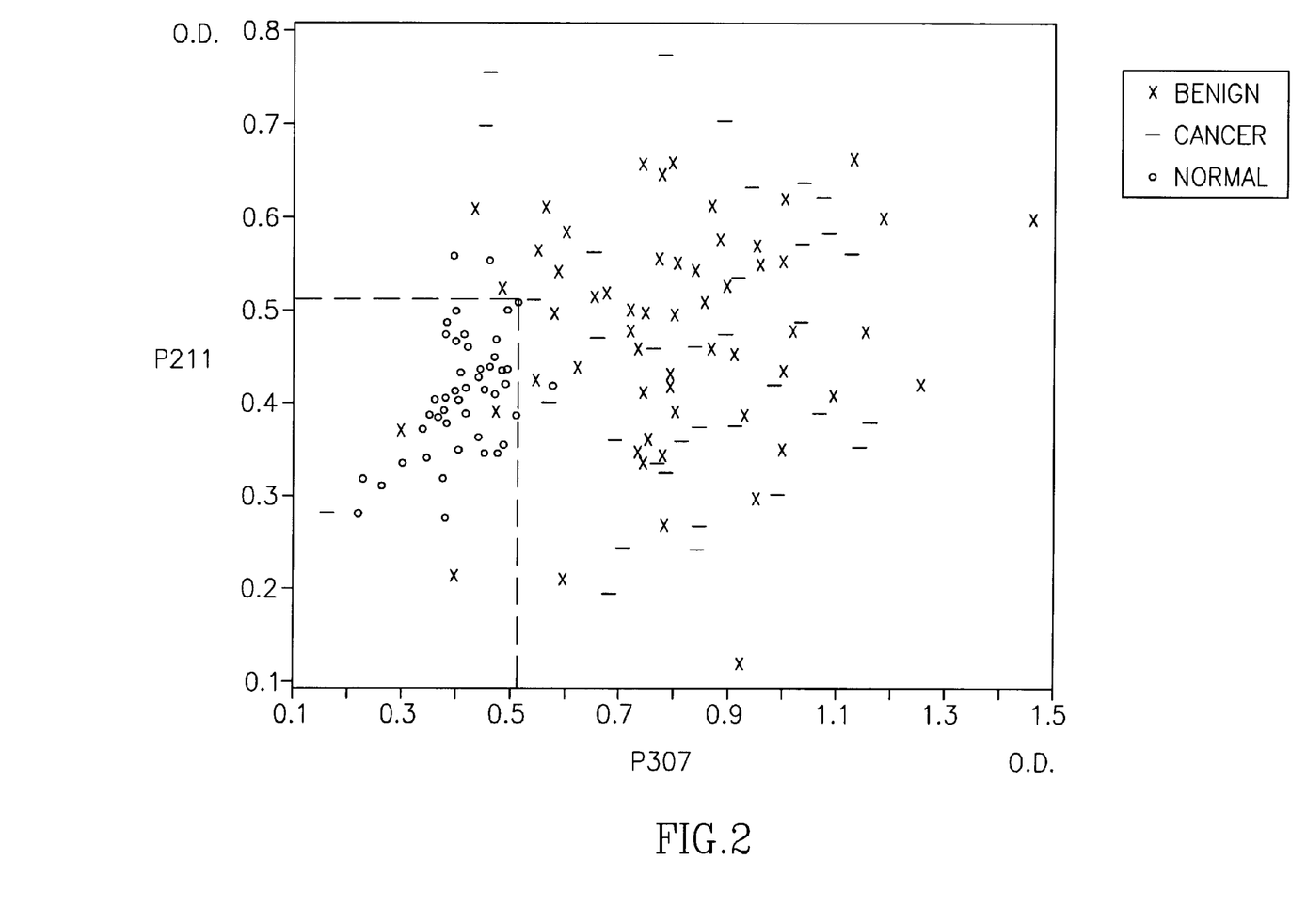
FIG. 2 P3 and P2 - Two dimensional analysis

FIG. 2: Two dimensional analysis—P3 and P2

One run of both peptides. The computer was able to frame (x: 5; y: 52) the normal (=healthy) samples (3–5 known high positive controls at a range of 0.6–0.65 O.D. were run together with 3–5 known negative sample controls at a range of 0.25–0.3 O.D., which are not shown in FIG. 2) By doing so only very few cancer samples were considered normal and vica versa.

Figure 3A:
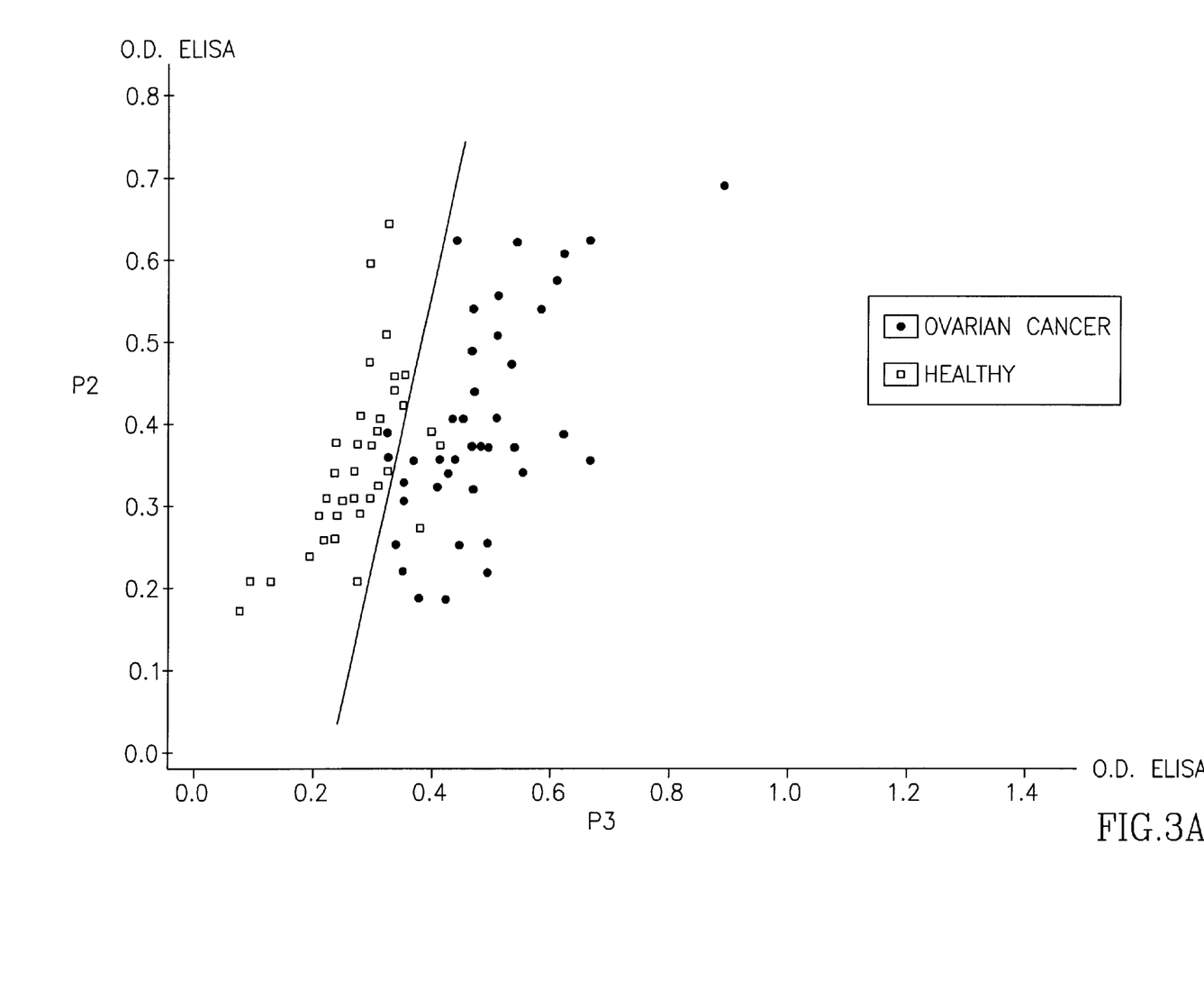
FIGS. 3A–3B P1 and P3, P2 and P3 - Two dimensional analysis
Figure 3B:
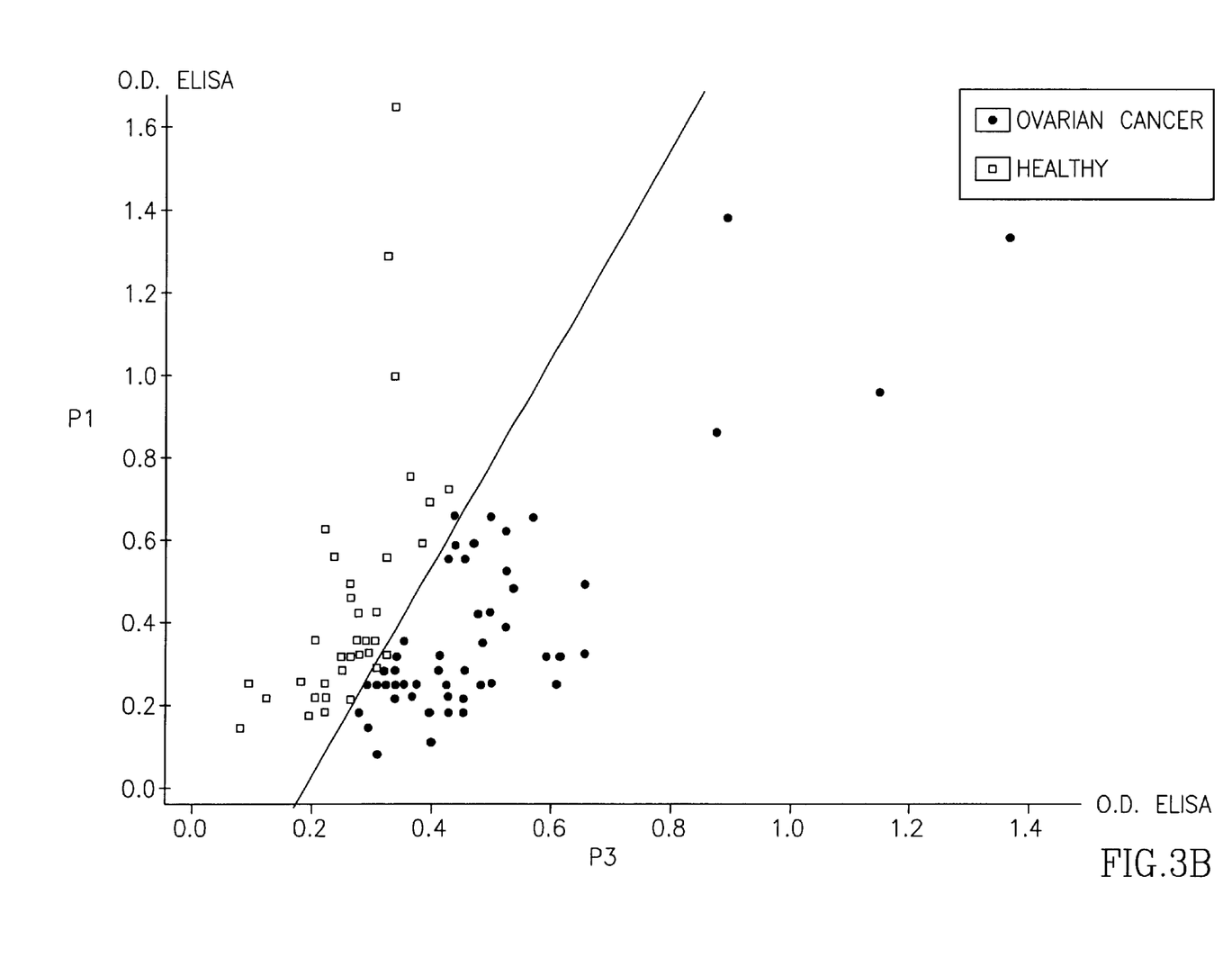

FIGS. 3A–3B: Two dimensional analysis P1 AND P3, AND P2 AND P3

The samples studied were run at groups of <100 each. Two-dimensional analysis of two different peptide ELISAs run on the same set of samples. FIG. 3A of P2 and P3 and FIG. 3B of P1 and P3 shows that a clear line devides the h=healthy patients from the c=cancer patients. The patients to the right of the line are those in which the immunologic profile indicates the presence of ovarian or breast cancer. While, patients to the left of the line indicates a patient is healthy. The ratio between the O.D. reading of P1 and P3, or P2 and P3 determines the diagnosis.

TABLE 2

Results of three dimensional linear classification

Classified into group.

| Group | Re-substitution | | | Cross-Validation | | |
|---|---|---|---|---|---|---|
| | Normal | Benign | Cancer | Normal | Benign | Cancer |
| 48 Normal | 41 | 7 | 0 | 40 | 8 | 0 |
| 56 Benign | 2 | 32 | 22 | 3 | 25 | 28 |
| 38 Cancer | 2 | 14 | 32 | 2 | 16 | 20 |

Table 2 shows the linear classification of the combined 3 peptides. As demonstrated there is a high resolution uing both methods of statistical claculation.

EXAMPLE 3

Early Detection Of Prostate Cancer

Prostate specific tumor antigen (PSA) rises markedly due to the tumor growth. It is not clear whether there are tumor antigenic/tumor antigenic differences between the PSA in the serum in normal levels and the PSA produced by the tumor or because of it. Based on other examples (such as the MUC-1 in breast cancer) there could be such differences. Then the detection of antibodies against it could serve as a follow-up of PSA from serum of prostate cancer patients will be used as tumor antigen peptides/segments form it, or cells from a cell line from the tumor . . . ).

Sera and supernatant fluid from new method cultures will be tested for PSA specific reactivity. It is expected that there will be higher antibody levels in the serum of some of the patients then in the population of normal controls, but a much higher proportion of them will have anti PSA antibodies in the culture fluid.

Virus encoded tumor antigens from tumor inducing viruses (both DNA and RNA viruses, even though these tumor antigens are more commonly found with relation to RNA viruses as fas as expression of the cell membrane.

For example gp70 (which is also found on chemically induced tumors) from the virus envelope glycoprotein. Purified gp70 will be used as tumor antigen (or defined peptides/segments form it, or infected cells expressing it). Sera and supernatant fluid form new method cultures will be tested for gp70 specific reactivity. It is expected that there will be higher antibody levels in the serum of some of the patients than in the population of normal controls, but a much higher proportion of them will have anti gp70 antibodies in the culture fluid.

EXAMPLE 4

Multiple Tumor Antigen Assay

An tumor antigen (on some type of a carrier) is inside the tube during the incubation period of the culture (blood culture).

The presence of the tumor antigen serves mainly as a "detector" and "binder" (for ligand) for the tumor antigen specific antibodies that are present (or being produced) in the culture. It could also serve at the same time as a specific stimulator (specific) of the specific segment of the immune process that is taking place in the tube.

The tumor antigen may be in the tube prior to blood drawn in (or cells added) or added at any time-point during the culture. (Thus it could be in contact during the culture days, hours or minutes). The tumor antigen can be attached to (or bound to): 1) The tube itself either above the level of the culture liquid, at the level of the culture liquid, or below the level of the culture liquid; 2) bound to a nitrocellulose strip; 3) bound to any synthetic carrier (plastic of all sorts); 4) bound to beads, microspheres, etc; 5) be part of a "dry chemistry" (or more exact "dry immunochemistry" system [closed or open]). The surfaces of all the above, (especially beads), can be smooth or grooved or in any other form of shape that will increase its surface area.

The tumor antigen can be bound to all the above carriers directly or via carriers, "arms" and other methods that put a distance between the Ag and the "carrier's" surface. The tumor antigen can be applied to the "carrier" at any shape or size: ring around the tube, a line, a dot, a shape of a + or + or P or any other letter or shape. The tumor antigen can be attached to the carrier at one given concentration or at several concentrations, (either as discreet "sites" or as a continuous (or gradient). The tumor antigen can be a few tumor antigens—as more than one tumor antigen can be applied to one tube (or carrier or bead or beads, etc.). The different tumor antigens can be applied together (as a mixture) or in group or individually. When applied to more than one spot, they can be applied using the same shape of mark or using a different one for each tumor antigen.

The detection of the antibodies that bind to the tumor antigen can be done by any of the "developing" and detection systems that are known to date (or that will be found later. The developing reagents can be in the tube initially or added at a later time. A very simple method will be to finish the development stage towards the end of the culture period or after the end of it all together. The development is either by direct binding of "tagged" antibodies or by competition assays. The "tag" can be an enzyme, a metal, a color colloid, (or fluorescent, lluminecent etc.)

What is claimed is:

1. A method for the detection of tumor antigen associated antibodies in a sample obtained from a subject, comprising the following steps:
   a) obtaining a whole blood sample from the subject;
   b) incubating the whole blood sample in a culture in the presence of a mitogen containing media, so as to induce polyclonal activation of lymphocytic cells to produce specific tumor antigen associated antibodies;
   c) exposing the resultant culture of step b) to a tumor antigen, thereby allowing an antigen-antibody immune complex to form; and
   d) detecting the presence of an antigen-antibody immune complex of step c); wherein the presence of antigen specific antibodies in indicative of the subject being with a tumor.

2. The method of claim 1, wherein the culture of step c) results in a supernatant, and the supernatant is exposed to an tumor antigen, thereby allowing an antigen-antibody immune complex to form.

3. The method of claim 1, wherein the culture of step c) results in a cellular fraction which is exposed to an antigen, thereby allowing an antigen-antibody immune complex to form.

4. The method of claim 1, wherein the mitogen activates lymphocytic cells.

5. The method of claim 4, wherein the mitogen is pokeweed mitogen, a lectin, a bacterial endotoxin, a tumor antigen, lipid A, or a lymphokine.

6. The method of claim 1, wherein the mitogen is pokeweed mitogen.

7. A method for screening a subject having cancer, comprising the following steps:
   a) obtaining a whole blood sample from the subject;
   b) incubating the whole blood sample in a culture in the presence of a mitogen containing media, so as to induce polyclonal activation of lymphocytic cells to produce specific tumor antigen associated antibodies;
   c) exposing the culture of step b) to an tumor antigen, thereby allowing an antigen-antibody immune complex to form; and
   d) detecting the presence of antigen-antibody immune complex of step c); wherein the presence of tumor antigen specific antibodies is indicative of the having cancer.

8. The method of claim 7, wherein the culture of step c) results in a supernatant, and the supernatant is exposed to an tumor antigen, thereby allowing an antigen-antibody immune complex to form.

9. The method of claim 7, wherein the mitogen activates lymphocytic cells.

10. The method of claim 9, wherein the mitogen is pokeweed mitogen, a lectin, a bacterial endotoxin, a tumor antigen, lipid A, or a lymphokine.

11. The method of claim 7, wherein the mitogen is pokeweed mitogen.

12. A kit for the detection of specific tumor antigen associated antibody from a subject, comprising: a container for collecting whole blood samples, wherein the container contains a media containing mitogen, effective to induce polyclonal activation of lymphocytic cells leading to antibody production and an assay for the detection of the specific tumor antigen associated antibody.

13. The kit of claim 12, wherein the assay is an enzyme linked immunosorbent assay, or an immunofluorescence assay.

14. The kit of claim 12, wherein the container is made of a plastic, glass, or metal material.

15. The kit of claim 14, wherein the container is a test tube or a flask.

16. The kit of claim 15, wherein the container is vacuum sealed.

17. The kit of claim 12, wherein an tumor antigen is bound to the container.

18. The kit of claim 17, wherein multiple tumor antigens are bound to the container.

* * * * *